(12) United States Patent
Jakubowicz

(10) Patent No.: US 10,031,085 B2
(45) Date of Patent: Jul. 24, 2018

(54) POINT OF CARE ANALYTICAL PROCESSING SYSTEM

(71) Applicant: Ortho-Clinical Diagnostics, Inc., Raritan, NJ (US)

(72) Inventor: Raymond F. Jakubowicz, Rush, NY (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 147 days.

(21) Appl. No.: 14/807,212

(22) Filed: Jul. 23, 2015

(65) Prior Publication Data

US 2016/0025639 A1    Jan. 28, 2016

Related U.S. Application Data

(60) Provisional application No. 62/028,439, filed on Jul. 24, 2014.

(51) Int. Cl.
  *G01N 21/75*  (2006.01)
  *G01N 21/78*  (2006.01)
  (Continued)

(52) U.S. Cl.
  CPC ............ *G01N 21/78* (2013.01); *B01L 3/5023* (2013.01); *B01L 3/50273* (2013.01); *B01L 9/52* (2013.01);
  (Continued)

(58) Field of Classification Search
  CPC ............ G01N 21/78; G01N 35/00029; G01N 33/48707; G01N 33/49; G01N 2035/0439;
  (Continued)

(56) References Cited

U.S. PATENT DOCUMENTS

| 3,992,158 A | 11/1976 | Przybylowicz et al. |
| 4,086,060 A | 4/1978 | Hermann, Jr. |

(Continued)

FOREIGN PATENT DOCUMENTS

| EP | 0 458 138 A2 | 11/1991 |
| EP | 0 867 724 B1 | 9/1998 |

(Continued)

OTHER PUBLICATIONS

International Search Report and Written Opinion for PCT/US2015/041917; dated: Oct. 9, 2015; 12 pages.

*Primary Examiner* — Dennis White
(74) *Attorney, Agent, or Firm* — K&L Gates LLP; Louis C. Cullman; Joseph Arand

(57) ABSTRACT

A point of care testing system includes a reader having an incubator disposed within a reader housing, the incubator having a rotor supported for rotation and having a plurality of circumferentially disposed slots. A drive mechanism is configured to rotate the rotor about a center axis A plurality of analytical test elements are sized for fitting in the slots of the incubator either manually or on demand. Each analytical test element commonly includes a support within a cartridge. The support retains at least one of a dry chemistry chip comprising a porous spreading layer disposed in stacked relation with at least one reagent layer or a lateral flow assay device wherein the plurality of test elements can assume a common form factor with multiplexed capability, and in which cartridges are preferably gated to enable random access processing.

14 Claims, 7 Drawing Sheets

(51) Int. Cl.
*B01L 3/00* (2006.01)
*B01L 9/00* (2006.01)
*G01N 33/487* (2006.01)
*G01N 33/49* (2006.01)
*G01N 35/00* (2006.01)
*G01N 21/77* (2006.01)
*G01N 35/04* (2006.01)

(52) U.S. Cl.
CPC ........ *B01L 9/527* (2013.01); *G01N 33/48707* (2013.01); *G01N 33/49* (2013.01); *G01N 35/00029* (2013.01); *B01L 2300/0681* (2013.01); *B01L 2300/0825* (2013.01); *B01L 2300/0864* (2013.01); *B01L 2400/0406* (2013.01); *B01L 2400/086* (2013.01); *G01N 2021/752* (2013.01); *G01N 2021/7759* (2013.01); *G01N 2035/00158* (2013.01); *G01N 2035/00356* (2013.01); *G01N 2035/0439* (2013.01)

(58) Field of Classification Search
CPC ..... G01N 2021/752; G01N 2021/7759; G01N 2035/00356; G01N 2035/00158; B01L 9/527; B01L 9/52; B01L 3/5023; B01L 3/50273; B01L 2300/0864; B01L 2300/0681; B01L 2400/086; B01L 2300/0825; B01L 2400/0406
See application file for complete search history.

(56) References Cited

U.S. PATENT DOCUMENTS

| | | |
|---|---|---|
| 4,142,853 A | 3/1979 | Terada et al. |
| RE30,627 E | 5/1981 | Bagshawe et al. |
| 4,269,803 A | 5/1981 | Jessop |
| 4,287,155 A | 9/1981 | Tersteeg et al. |
| 4,296,070 A | 10/1981 | Montalto et al. |
| 4,299,796 A | 11/1981 | Hogen Esch |
| 4,430,299 A | 2/1984 | Horne |
| 4,512,952 A | 4/1985 | Blanding et al. |
| 4,676,951 A | 6/1987 | Armes et al. |
| 4,678,752 A | 7/1987 | Thorne et al. |
| 4,774,055 A | 9/1988 | Wakatake et al. |
| 4,797,257 A | 1/1989 | Shaw |
| 4,815,978 A | 3/1989 | Mazza et al. |
| 4,931,402 A | 6/1990 | Abplanalp |
| 4,933,291 A | 6/1990 | Daiss et al. |
| 4,965,049 A | 10/1990 | Lillig et al. |
| 5,059,393 A | 10/1991 | Quenin et al. |
| 5,244,633 A | 9/1993 | Jakubowicz et al. |
| 5,260,872 A | 11/1993 | Copeland et al. |
| 5,314,825 A | 5/1994 | Weyrauch et al. |
| 5,324,481 A | 6/1994 | Dunn et al. |
| 5,326,398 A | 7/1994 | Kelley et al. |
| 5,332,549 A | 7/1994 | MacIndoe, Jr. |
| 5,374,395 A | 12/1994 | Robinson et al. |
| 5,380,487 A | 1/1995 | Choperena et al. |
| 5,381,487 A | 1/1995 | Shamos |
| 5,428,470 A | 6/1995 | Labriola, II |
| 5,441,895 A | 8/1995 | Jakubowicz et al. |
| 5,480,484 A | 1/1996 | Kelley et al. |
| 5,523,056 A | 6/1996 | Miller |
| 5,525,298 A | 6/1996 | Anami |
| 5,525,514 A | 6/1996 | Jacobs et al. |
| 5,575,976 A | 11/1996 | Choperena et al. |
| 5,658,799 A | 8/1997 | Choperena et al. |
| 5,679,309 A | 10/1997 | Bell |
| 5,693,292 A | 12/1997 | Choperena et al. |
| 5,736,403 A | 4/1998 | Riall et al. |
| 5,741,708 A | 4/1998 | Carey et al. |
| 5,747,666 A | 5/1998 | Willis |
| 5,753,512 A | 5/1998 | Riall et al. |
| 5,787,015 A | 7/1998 | Aldridge et al. |
| 5,882,596 A | 3/1999 | Breeser et al. |
| 5,885,533 A | 3/1999 | Savage et al. |
| 5,965,447 A | 10/1999 | Sekiyama et al. |
| 5,968,329 A | 10/1999 | Anderson et al. |
| 5,980,830 A | 11/1999 | Savage et al. |
| 5,983,734 A | 11/1999 | Mathur et al. |
| 6,013,528 A | 1/2000 | Jacobs et al. |
| 6,066,243 A | 5/2000 | Anderson et al. |
| 6,190,617 B1 | 2/2001 | Clark et al. |
| 6,372,542 B1 | 4/2002 | Martin et al. |
| 6,592,822 B1 | 7/2003 | Chandler |
| 6,733,682 B1 | 5/2004 | Björkman et al. |
| 6,811,736 B1 | 11/2004 | Ohman et al. |
| 6,845,327 B2 | 1/2005 | Lauks |
| 6,884,370 B2 | 4/2005 | Öhman et al. |
| 7,141,213 B1 | 11/2006 | Pang et al. |
| 7,267,798 B2 | 9/2007 | Chandler |
| 7,381,370 B2 | 6/2008 | Chow et al. |
| 7,384,600 B2 | 6/2008 | Burns et al. |
| 7,431,883 B2 | 10/2008 | Bell |
| 7,458,483 B2 | 12/2008 | Luoma, II |
| 7,670,554 B2 | 3/2010 | Chow et al. |
| 7,816,090 B2 | 10/2010 | Jacobs |
| RE41,946 E | 11/2010 | Anderson et al. |
| 7,855,084 B2 | 12/2010 | Jakubowicz et al. |
| 7,897,337 B2 | 3/2011 | Macioszek et al. |
| 7,968,051 B2 | 6/2011 | Oonuma |
| 8,008,066 B2 | 8/2011 | Lair et al. |
| 8,025,854 B2 | 9/2011 | Ohman et al. |
| 8,038,942 B2 | 10/2011 | Pang et al. |
| 8,128,871 B2 | 3/2012 | Petruno et al. |
| 8,257,650 B2 | 9/2012 | Chow et al. |
| 8,431,079 B2 | 4/2013 | Rosenberg et al. |
| 8,501,461 B2 | 8/2013 | Knight et al. |
| 8,535,624 B2 | 9/2013 | Luoma, II |
| 2001/0019842 A1 | 9/2001 | Kitamura et al. |
| 2002/0098116 A1 | 7/2002 | Sugaya et al. |
| 2002/0155590 A1 | 10/2002 | Gebrian et al. |
| 2003/0017613 A1* | 1/2003 | Jakubowicz ..... G01N 35/00029 436/43 |
| 2003/0054542 A1 | 3/2003 | Burns et al. |
| 2003/0235919 A1 | 12/2003 | Chandler |
| 2005/0069454 A1 | 3/2005 | Bell |
| 2006/0204997 A1 | 9/2006 | Macioszek et al. |
| 2006/0240541 A1 | 10/2006 | Petruno et al. |
| 2006/0285996 A1 | 12/2006 | Ohman et al. |
| 2007/0059209 A1 | 3/2007 | Pang et al. |
| 2008/0145939 A1 | 6/2008 | Jakubowicz et al. |
| 2009/0129979 A1 | 5/2009 | Kegelman et al. |
| 2009/0148345 A1 | 6/2009 | Hamazumi et al. |
| 2010/0075336 A1 | 3/2010 | Knight et al. |
| 2011/0183352 A1 | 7/2011 | Mpock et al. |
| 2012/0094276 A1 | 4/2012 | Buchanan |
| 2012/0156112 A1 | 6/2012 | Sprague et al. |
| 2013/0280698 A1* | 10/2013 | Propper ............ G01N 33/5302 435/5 |
| 2013/0330713 A1 | 12/2013 | Jakubowicz et al. |
| 2014/0141527 A1 | 5/2014 | Ding et al. |
| 2014/0272941 A1 | 9/2014 | Gunnerson et al. |
| 2014/0275866 A1 | 9/2014 | Gunnerson et al. |

FOREIGN PATENT DOCUMENTS

| | | |
|---|---|---|
| EP | 1 099 114 B1 | 5/2001 |
| EP | 1 393 068 B1 | 3/2004 |
| EP | 1 614 470 B1 | 1/2006 |
| WO | WO 99/58955 | 11/1999 |
| WO | WO 00/05581 | 2/2000 |
| WO | WO 03/103835 A1 | 12/2003 |
| WO | WO 2005/089082 A2 | 9/2005 |
| WO | WO 2005/118139 A1 | 12/2005 |
| WO | WO 2006/137785 A1 | 12/2006 |
| WO | WO 2007/001084 A1 | 1/2007 |
| WO | WO 2007/149042 A1 | 12/2007 |
| WO | WO 2010/120786 A1 | 10/2010 |

* cited by examiner

POINT OF CARE ANALYTICAL PROCESSING SYSTEM

CROSS REFERENCE TO RELATED APPLICATIONS

This application claims priority under applicable portions of 35 U.S.C. § 119 to U.S. Patent Application Ser. No. 62/028,439, filed Jul. 24, 2014 and entitled: POINT OF CARE ANALYTICAL PROCESSING SYSTEM, the entire contents of which is incorporated by reference herein.

TECHNICAL FIELD

This application relates generally to the field of diagnostic clinical devices and more specifically to a point of care analytical system capable of handling a plurality of analytical test elements, including individual test elements which enable multiple number of tests to be conducted thereon.

BACKGROUND

Point of Care (POC) testing provides rapid diagnostic results using simple analytical readers and test elements proximate the patient, the test elements typically being disposed in cartridges in which a plurality of test elements can be stored. The setting for these apparatuses may be a single practice physician's office, a group practice, an emergency care center, or may further include hospital settings including bedside, emergency room, intensive care, or other locations, each setting needing rapid turnaround of test results. Typical point of care systems are limited by walk up access/availability and throughput. More specifically, these systems typically deploy one (1) patient or test at a time for processing. As a result, and once a test element is inserted into the reader device, another test cannot be initiated until the previous test has been completed. For some immunoassay measurements, the time for completing a test can be as long as 12 minutes, or longer. Readers are also limited typically to a particular test measurement method (i.e., fluorescence, photometric or colorimetric measurements) and have a somewhat limited menu of tests that can be run by the instrument. The reader is typically locked until a test has been completed or aborted and since current POC readers are dedicated to only a single assay method, a pervasive need in the field has since developed for deploying multiple readers to meet menu and throughput demands. Each reader further requires quality control (QC) and routine maintenance. With single sample processing, testing can easily become backlogged, therefore reducing the benefit of point of care testing since in many situations a hospital laboratory is available to conduct the test. A solution to the above needs that provides test flexibility (i.e., a broader available menu of tests and the ability to process multiple test types), reduces testing backlogs and delivers a significant cost reduction (in terms of the reader, calibration/control, maintenance, and overall support costs), when compared to deployment of multiple readers, is critical to meeting the needs of point of care diagnostics.

BRIEF DESCRIPTION

Therefore and according to one aspect, a point of care analytical testing system is provided, the testing system comprising:
a point of care reader comprising:
a housing including an interior;
an incubator disposed in the housing interior and having a rotor configured for rotation and having a plurality of circumferentially disposed slots;
a drive mechanism for rotating the rotor about a center axis; and
at least one measurement device and
a plurality of analytical test elements, each analytical test element being sized for fitting in a slot of the incubator and comprising:
a support; and
a cartridge configured for retaining the support, the cartridge including an upper cover portion and a lower cover portion and wherein the support retains at least one of a dry chemistry chip comprising a porous spreading layer disposed in stacked relation with at least one reagent layer or a lateral flow assay device.

According to one version, at least one of the analytical test elements is configured to run a plurality of tests. The cartridge can include at least one port aligned with a sample receiving zone for applying a quantity of sample to a sample receiving zone of a support.

According to another version, at least one of the analytical test elements can include each of a lateral flow assay device as well as at least one dry chemistry chip. The cartridge can include a port aligned with a sample receiving zone of the support in which the sample receiving zone is common to each of the lateral flow assay device and the at least one dry chemistry chip.

Each of the foregoing analytical test elements is defined by a common cartridge, enabling each of these test elements to be used in a single reader.

In at least one embodiment, the reader can include a display. The display can include a touch screen creating a user interface for operating the analytical system.

In one embodiment, an analytical test element used in the herein described system includes a lateral flow assay device and at least one dry chemistry test chip or support which is disposed commonly on a single substrate. In another version, a plurality of dry chemistry test chips can be disposed on a single substrate.

The reader can include a metering station disposed in relation to the incubator, the metering station including a metering device configured to provide a quantity of sample to a supported analytical test element. In at least one version, the metering station can include an infusion pump configured to apply pressure to a sample supply on the analytical test element and selectively causing sample to be applied to a sample receiving area of the test element.

The reader can include a plurality of measurement or read stations, each station having at least one measurement device aligned with the slots of the rotatable rotor of the incubator. In one version, the read station can include multiple detection instruments, for example a fluorimeter and a reflectometer.

According to at least one version, the reader can be configured for direct loading of analytical test elements or at least one analytical test element can be placed in a port provided on the reader in which a test element can be loaded at a later time for testing. The analytical test elements can be configured with gated cartridges, such that actuation and conduction of tests can be done via random access.

In accordance with another aspect, an analytical test element is provided comprising:
a support; and
a cartridge configured for retaining the support, the cartridge including an upper cover portion and a lower cover portion and in which the support retains at least one dry chemistry chip comprising a porous spreading layer disposed in stacked relation with at least one reagent layer.

The cartridge, according to at least one version, can further include a sample supply disposed on the cartridge, the supply being configured such that a retained quantity of sample is prevented from being moved to the at least one supported analytical test element until specifically acted upon, for example, by a device contained within the reader. According to at least one embodiment, a pump or similar means can be applied to the sample supply of the cartridge to selectively move the contained sample via delivery and transport features for conduction of test(s) In accordance with yet another aspect, there is provided a method for increasing the throughput of a point of care reader, said method comprising:

configuring the reader with an incubator having a rotor, the rotor being supported for rotation about a center axis and having a plurality of circumferentially disposed slots;

providing a drive mechanism for rotating the rotor;

providing at least one measurement apparatus in relation to at least one of the disposed slots; and providing a plurality of analytical test elements for loading into the reader, said plurality of analytical test elements comprising a cartridge sized for receipt by a disposed slot of the incubator and retaining a support that includes at least one dry chemistry chip.

In one version, the analytical test element includes at least one lateral flow assay device, the lateral flow assay device including a sample receiving zone, at least one reagent zone and an absorbing zone, each of the zones being disposed along a fluid flow path.

In one version, at least a portion of the fluid flow path includes a plurality of projections, the projections extending from the substrate and having heights, diameters and reciprocal center to center spacing between the projections that enable capillary flow along the defined fluid flow path.

In at least one version, the plurality of analytical test elements can be configured with a sample supply or retainer in which the reader is configured to selectively actuate a analytical test element by engaging the sample supply and moving the sample under capillary action or other driving force to a sample receiving area of the test element, which then further directs the sample for purposes of testing.

According to at least one embodiment, the herein described point of care analytical system is configured to conveniently process whole blood (or other samples) test elements in a random access sequence using an incubated positioning transport that provides access to entry and exit ports, read or other measurement stations, and fluidic actuators of the system. One feature of the system is the ability of the reader to process more than one test element at a time, allowing efficient work flow and faster turnaround time. Test throughput is governed by the incubation time of the test (e.g., 5-15 minutes), the number of available rotor positions in the incubator (e.g., 4, 8 positions, although the number could be varied higher or lower) and the number of multiplexed tests that can be performed per test element (e.g., 1-8 tests).

The foregoing apparatus is an ideal solution, for example, for emerging markets where access to low cost testing is problematic. The increased throughput provided by this system is sufficient for a small laboratory and with gated cartridges to enable random access, this can be easily handled by one operator. With this capability, a single reader can completely meet the testing need of an point of care environment, allowing more than one test to be conducted without creating a bottleneck, as produced in individual sample testing.

In one version, the analytical test element can support between about 1 to about 8 separate tests.

Advantageously, the herein described analytical system introduces an analytical test element having a consistent/common assay form factor, enabling the measurement of analytes in whole blood, plasma, serum, urine or other body fluids of interest.

Moreover, the herein described analytical test element and system enables small sample sizes. For example, small whole blood samples as low as 25 μL can be used, although the system can be configured to easily accept a larger range (e.g., 10-200 μL).

Multiple chemistry methods can be employed with the ability to process general chemistry and immunoassays simultaneously with true random access processing due to the system design and use of gated cartridges (test elements) that enable selective sample metering.

The system permits test cartridges that enable a test or multiple tests within the same cartridge for efficient operation for a wide range of menus.

In addition to the modularity that can be provided in regard to the herein described system (for example, various measurement modules can be interchanged), the system can be configured to operate automatically once a test element has been loaded into the reader. A gated consumable (sample not delivered until actuated by the analyzer) is assumed since timing will be crucial when processing more than one consumable at a time and must be under control of the reader, and wherein on demand processing is provided. A touch screen user interface (UI) can be provided with the herein described system to provide simple information entry and retrieval.

Other elements, such as wash modules, can also be provided depending on the tests to be performed and/or the test devices using a common form factor applicable to all contained analytical test elements for the herein designed system.

These and other features and advantages will be readily apparent from the following Detailed Description, which should be read in conjunction with the accompanying drawings.

DETAILED DESCRIPTION

Figure 1:
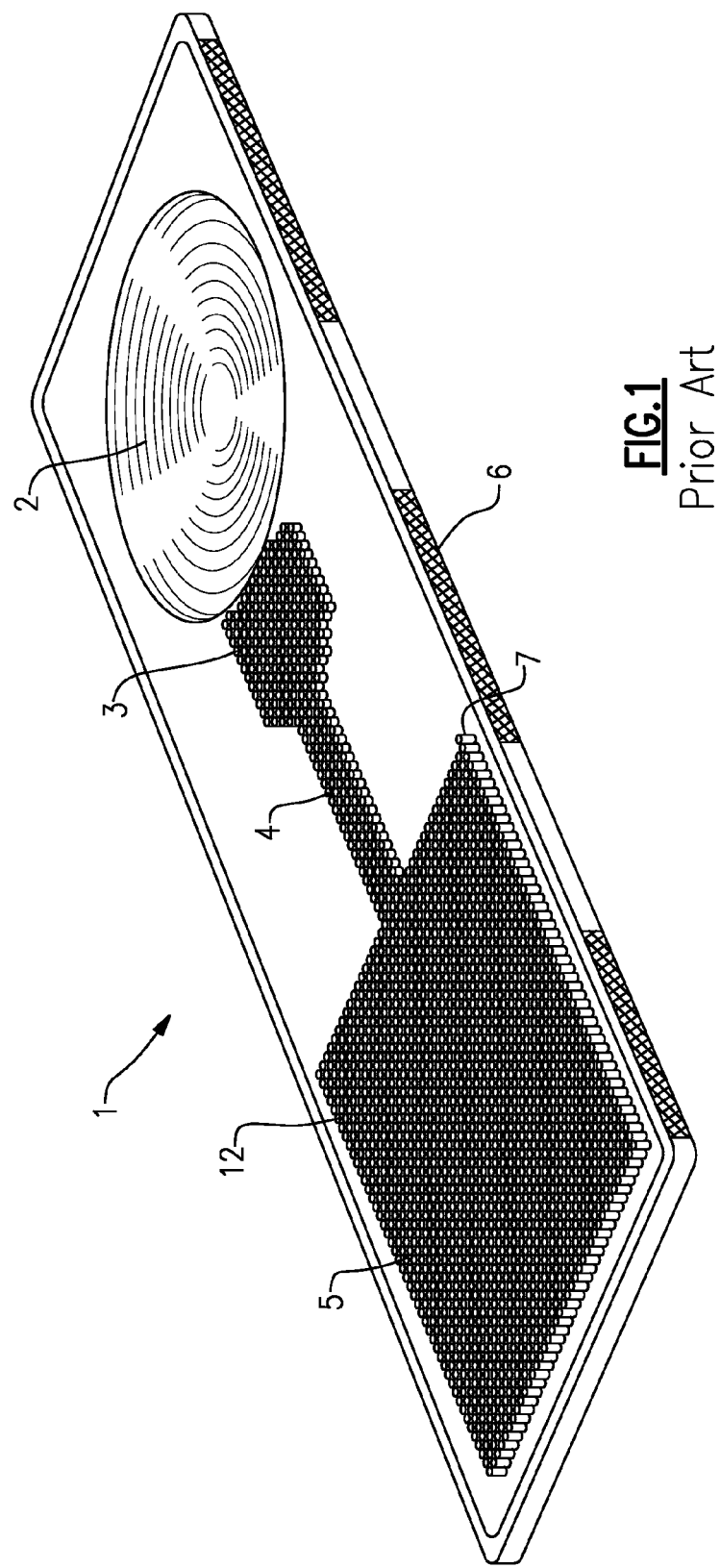
FIG. 1 is a top perspective view of a lateral flow assay device made in accordance with the prior art.

The following description relates to a point of care system that includes a compact reader, as well as various embodiments of an analytical test element that can be used in conjunction with the reader. Certain terms are used throughout this discussion in order to provide a suitable frame of reference in regard to the accompanying drawings. These terms which include "top", "bottom", "upper", "lower", "above", "below", "distal", "proximal" and the like are not intended to narrow the scope of the inventive concepts, including those of the appended claims, unless so specifically indicated.

In addition, the drawings as provided are intended to clearly illustrate the salient features of the claimed and described invention. To that end, these drawings may not necessarily be to scale and dimensions should not be overly relied upon by the reader for purposes of interpretation.

As used in this application, including the appended claims, the singular forms "a", "an" and "the" are intended to include plural referents unless the context clearly indicates otherwise.

The term "about" as used in this specification is used in connection with a numerical value to denote a level of accuracy, which is familiar and acceptable to a person skilled in the art. The interval governing this term is preferably ±20%.

In terms of defining certain of the terms that follow, the term "analyte" is used as a synonym of the term "marker" and intended to minimally encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The term "sample" as used herein refers to a volume of a liquid, solution or suspension, intended to be subjected to qualitative or quantitative determination of any of its properties, such as the presence or absence of a component, the concentration of a component, etc. Typical samples in the context of this application as described herein can include human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the sample tissue has been processed into a liquid, solution or suspension to reveal particular tissue components for examination. The embodiments of the present application, as intended, are applicable to all bodily samples, but preferably to samples of whole blood, urine or sputum.

In other instances, the sample can be related to food testing, environmental testing, bio-threat or bio-hazard testing, etc. The foregoing, however, represents only a small example of samples that can be used for purposes of the present invention.

In the present invention, any determinations based on lateral flow of a sample and the interaction of components present in the sample with reagents present in the device or added to the device during the procedure and detection of such interaction, either quantitatively or qualitatively, may be for any purpose, such as diagnostic purposes. Such tests are often referred to as "lateral flow assays".

Examples of diagnostic determinations include, but are not limited to, the determination of analytes, also referred to synonymously as "markers", specific for different disorders, e.g., chronic metabolic disorders, such as blood glucose, blood ketones, urine glucose, (diabetes), blood cholesterol, (atherosclerosis, obesity, etc); markers of other specific diseases, e.g., acute diseases, such as coronary infarct markers (e.g., tropinin-T, NT-ProBNP), markers of thyroid function (e.g., determination of thyroid stimulating hormone (TSH)), markers of viral infections (the use of lateral flow immunoassays for the detection of specific viral antibodies), etc, other cardiac indicators, general chemistry, electrolytes, lipid panels, and the like.

Yet another important field is the field of companion diagnostics in which a therapeutic agent, such as a drug, is administered to an individual in need of such a drug. An appropriate assay is then conducted to determine the level of an appropriate marker to determine whether the drug is having its desired effect. Alternatively, the assay device usable with the present invention can be used prior to the administration of a therapeutic agent to determine if the agent will help the individual in need.

Yet another important field is that of drug tests, for easy and rapid detection of drugs and drug metabolites indicating drug abuse; such as the determination of specific drugs and drug metabolites in a urine or other sample.

The term "lateral flow device" as discussed throughout this application herein refers to any device that receives a fluid, such as sample, and includes a laterally disposed fluid transport or fluid flow path along which various stations or sites (zones) are provided for supporting various reagents, filters, and the like through which sample traverses under the influence of capillary or other applied forces and in which lateral flow assays are conducted for the detection of at least one analyte (marker) of interest.

The terms "thin film chemistry device", "thin film chip", "dry chemistry device" or dry chemistry chip" as discussed throughout this application herein refers to an accumulation of integral stacked layers that include a porous spreading layer and at least one reagent layer, as discussed in U.S. Pat. No. 3,992,158, the entire contents of which are herein incorporated by reference.

The terms "automated clinical analyzer", "clinical diagnostic apparatus", or "clinical analyzer", refer to any apparatus enabling the scheduling and processing of various analytical test elements, including those employing lateral flow assay devices and dry chemistry or thin film chemistry, as discussed herein and in which a plurality of test elements can be initially loaded for processing. This apparatus further includes a plurality of components/systems configured for loading, incubating and testing/evaluating a plurality of analytical test elements in automated or semi-automated fashion and in which test elements are automatically dispensed from at least one contained storage supply, such as a cartridge or other apparatus, without user intervention. As discussed herein and based on a common form factor, the above assemblages can further include a "point of care" version.

The term "testing apparatus" as used herein refers to any device or analytical system that enables the support, scheduling and processing of lateral flow assay devices and dry slide elements or a combination of lateral flow devices and dry slide analytical test elements. A testing apparatus can include an automated clinical analyzer or clinical diagnostic apparatus such as a bench, table-top or main frame clinical analyzer, as well as point of care (POC) and other suitable devices. For purposes of this definition, the testing apparatus may include a plurality of components/systems for loading and testing/evaluating of a plurality of analytical test element, each of which may include at least one lateral flow device and/or at least one dry chemistry test element, including various detection instruments for detecting the presence of at least one detectable signal of the plurality of analytical test elements.

The terms "zone", "area" and "site" as used throughout this application, including the appended claims, define parts of a fluid flow path on a substrate, either in prior art devices or in at least one lateral flow assay device according to an embodiment of this invention. The term "layer" is similarly used to define parts of dry slide or thin film analytical test elements according to at least one embodiment of the invention.

The term "gated" as used herein refers to a feature of the analytical test elements in which a sample is applied to a collection port or similar holding or supply feature on the cartridge body. The sample is not directed to the testing features of the test element, such as a contained support, until specifically acted upon by a device that causes sample to be moved from the collection port to a sample receiving area or zone of the test element, thereby actuating or activating the analytical test element selectively.

The terms "reaction" is used to define any reaction, which takes place between components of a sample and at least one reagent or reagents on or in the substrate, or between two or more components present in the sample. The term "reaction" is in particular used to define the reaction, taking place between an analyte (marker) and a reagent as part of the qualitative or quantitative determination of the analyte.

The terms "substrate" or "support", as used herein, refers to the carrier or matrix to which a sample is added, and on or in which the determination is performed, or where the reaction between analyte and reagent takes place.

The term "detection" and "detection signal" as used herein, refers to the ability to provide a perceivable indicator that can be monitored either visually and/or by machine vision, such as a detection instrument.

The term "process-related event" refers herein to an event that occurs prior to the detection of analyte in an analytical test element, as described herein, such as, for example, the addition of at least one reagent, such as a wash reagent in a lateral flow assay device.

For purposes of this description throughout, the term "conjugate" means any moiety bearing both a detection element and a binding partner.

For purposes of this description, a "detection element" is an agent which is detectable with respect to its physical distribution and/or the intensity of the signal it delivers, such as but not limited to luminescent molecules (e.g., fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element, also referred to as a label, is preferably chosen from chromophores, fluorophores, radioactive labels and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but not limited to, fluoroceins, Cy3, Cy5 and the like. Suitable chemiluminescent labels include, but are not limited to luminol, cyalume and the like.

Similarly, radioactive labels are commercially available, or detection elements can be synthesized so that they incorporate a radioactive label. Suitable radioactive labels include but are not limited to radioactive iodine and phosphorus; e.g., $^{125}$I and $^{32}$P.

Suitable enzymatic labels include, but are not limited to horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or an amount of an analyte. For example, in a "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Referring to FIG. 1, a lateral flow assay device in accordance with the known art is defined by a substrate 6, which is substantially planar and further defined by an upper or top surface 7. A plurality of projections 12, such as microposts or pillars extend upwardly from the substrate 6 to the top surface 7. These projections 12 are disposed in spaced relation to one another and are dimensioned in terms of their height and diameter as well as their reciprocal center to center spacing to one another so as to induce lateral capillary force upon a liquid sample that is introduced into the assay device 1. The assay device 1 is further defined by a plurality of areas or zones that are linearly disposed along at least one fluid flow path, each of the zones including the projections 12 to facilitate fluidic flow. More specifically, the assay device 1 includes a sample receiving zone 2 adjacent at least one reagent zone 3, the latter zone 3 having a detection material such as a detection conjugate that is coated, impregnated or otherwise applied or deposited onto the projections 12. According to this design, a flow channel 4 extending from the reagent zone 3 may include at least one detecting zone and/or another reagent zone, depending on the type of assay being conducted, the flow channel 4 extending to an absorbing or wicking zone 5 that is disposed at the opposing end of the fluid flow path relative to the sample receiving zone 2. Additional specifics relating to the design of this lateral flow assay device 1 can be found in U.S. Pat. No. 8,025,854 B2, WO2003/103835, WO2005/089082, WO2005/118139, WO2006/137785, the contents of each of the above documents being herein incorporated by reference.

In terms of overall operation, a fluidic sample such as whole blood is initially applied to the sample receiving zone 2 through a cover (not shown) or through direct application using a pipette (not shown) or other dispensing means, wherein sample is caused to move along the fluid flow path through the at least one reagent zone 3 based on the capillary pressure exerted by the plurality of projections 12. The sample encounters the detection material deposited in the reagent zone 3 which, upon contact, therewith produces a detectable signal, such as a color change that is visually perceivable. The sample along with dissolved detection material, continues to migrate through the assay device 1 along the fluid flow path through the flow channel 4 having at least one detection zone or area (not shown), enabling access by a measurement instrument, such as a fluorimeter, and wherein the sample continues to move along the fluid flow path to the absorbing zone 5. After a sufficient time to fill the absorbing zone 5, the assay is considered to be complete and a detectable result can be obtained using the detection instrument (not shown) at the at least one detection zone.

Figure 2:
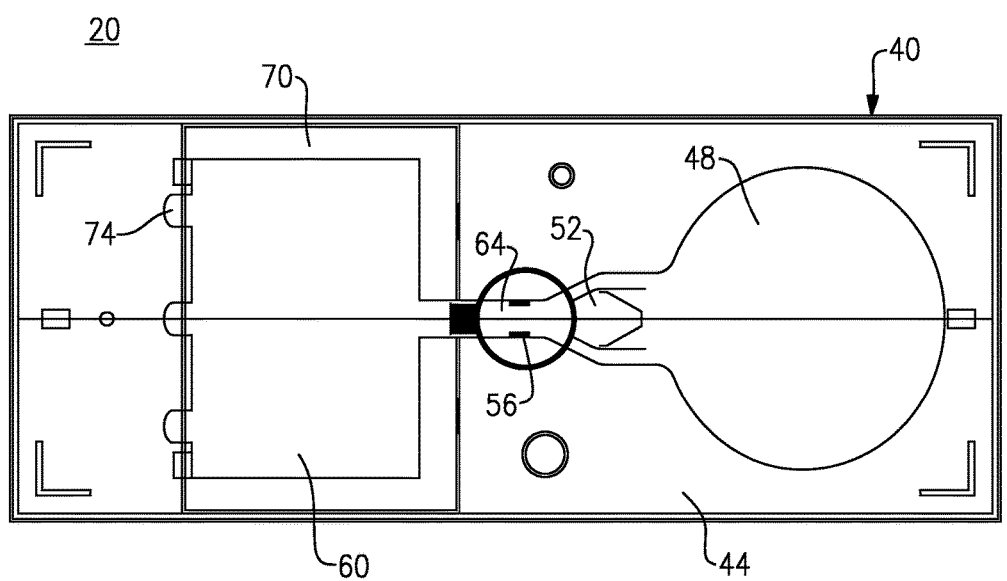
FIG. 2 is a top plan view of another lateral flow assay device.

Referring to FIG. 2, another example or version of a lateral flow assay device 20 includes a planar substrate 40, which can be made from a moldable plastic or other suitable non-porous material. A preferred material is Zeonor, which is an optically transparent plastic material that is capable of being molded. The substrate 40 is defined by a top or upper surface 44, which is further defined by a plurality of discrete zones or areas including a sample receiving zone 48, a reagent zone 52, a plurality of detection zones 56 (only one being shown) and an absorbing or wicking zone 60. According to this known device design, each of the above-noted zones are fluidically connected to one another in a linear fashion along a defined fluid flow path that further includes a flow channel 64 and in which a plurality of projections (not shown), similar to those provided in the assay device 1, FIG. 1, are disposed within at least one of the zones and/or the flow channel 64, the projections extending upwardly to the upper surface 44 of the substrate 40.

As in the preceding discussion relating to the assay device 1, FIG. 1, the projections of the instant assay device 20 are also defined by height and diameter dimensions, as well as reciprocal center to center spacings between the configured projections that create or induce lateral capillary flow in regard to an introduced fluid without the need for additional structure (i.e., side walls, cover or lid), or the application of any externally applied forces. According to this design, the defined fluid flow path is at least partially open. By "open" what is meant is that there is no cover or lid which is maintained at a distance that would contribute to capillary flow. Thus a lid, if present as physical protection for the fluid flow path and the assay device 20, does not contribute to the capillary flow produced along the fluid flow path. In this known assay device 20, a hydrophilic foil or tape cover 70 is adhesively or otherwise applied to the top of the projections in the wicking zone 60 in order to increase fluid flow in the assay device 20 and in which a plurality of vents or vent areas 74 are further defined in the hydrophilic foil or tape layer 70. An open lateral fluid flow path is described including the defined projections in the following published applications: WO2003/103835, WO2005/089082; WO2005/118139; WO2006/137785; and WO2007/149042, as well as U.S. Ser. No. 14/081,467, each of which are herein incorporated by reference in their entireties. More specifically, the extending projections each have a height (H), diameter (D) and a distance or distances between the projections (t1, t2) such that lateral capillary flow of an applied fluid, such as plasma, preferably human plasma, can be achieved. These relationships are further discussed in US Patent Application Publication No. 2006/0285996, which is further incorporated by reference in its entirety.

In use, the assay device 20 operates similarly in principle to the assay device 1, FIG. 1, in which a sample is applied to a sample receiving zone 48, such as through a port provided on a cover (not shown) and is wetted to the projections of the sample receiving zone 48. This contact of fluid causes sample to move under capillary force from the sample receiving zone 48 to the reagent zone 52 containing the deposited detection material. When wetted by the sample, the detection material supported in the reagent zone 52 reacts with the sample and dissolves, thereby producing a visually perceivable (colored) signal. The sample and the dissolved detection material advance along the defined fluid flow path and more specifically along the flow channel 64 under capillary force into the absorbing zone 60. When the absorbing zone 60 is filled with fluid, the assay is assumed to be completed and the assay results can be taken by a suitable detection instrument (e.g., a fluorimeter) relative to the at least one detection zone 56. As noted, the hydrophilic foil or tape cover is attached to the top of the projections in the absorbing zone of this device 20, the cover assisting in the capillary force to draw sample along the defined fluid flow path. Preferably, the hydrophilic cover 70 is provided over the entire absorbing zone 60 in which the vent areas 74 are disposed at a rear end of the absorbing zone 60. The foregoing assay device 20, including the substrate 40 and related sections of the defined fluid flow path is herein referred to throughout as a "lateral flow assay device".

Figure 3:
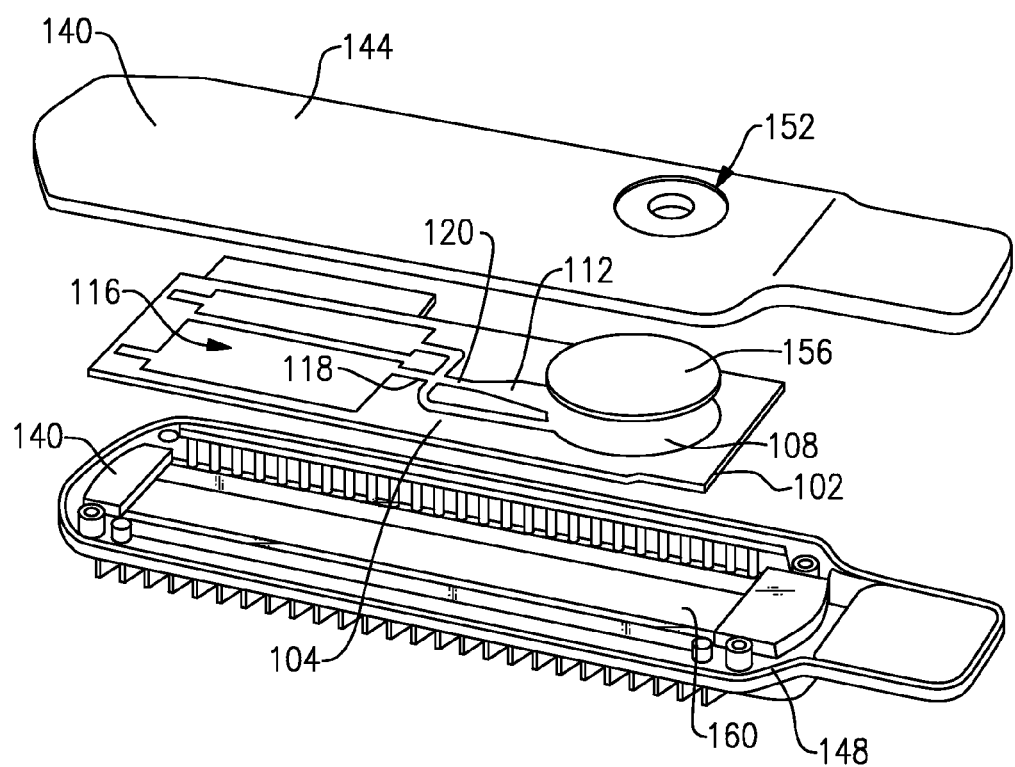
FIG. 3 is an exploded assembly view of a cartridge retaining the lateral flow assay device of FIG. 2.

Referring to FIG. 3, the foregoing version of a lateral flow assay device or an equivalent version, herein labeled with reference numeral 100, can be suitably supported within a cartridge 140 to define an analytical test element. As in the preceding, the lateral flow assay device 100 comprises a substrate or support 102, which is preferably planar and has a defined top or upper surface 104 further defined by a plurality of zones or areas that are disposed along a defined fluid flow path. These zones include a sample receiving zone 108 disposed at one end of the defined fluid flow path and a reagent zone 112 downstream but adjacent to the sample receiving zone 108 and fluidically connected therewith. An absorbing or wicking zone 116 is disposed at the opposite end of the fluid flow path relative to the sample receiving zone 108. The absorbing zone 116 and the reagent zone 112 are interconnected by a flow channel 120, which may further include at least one detection zone 118. A quantity of a detection material (not shown) that is configured to react with the sample is applied or otherwise deposited to the reagent zone 112. According to this exemplary structure, each of the zones 108, 112, 116 and flow channel 120 comprise a plurality of projections (not shown), such as those previously shown in FIG. 1, that are suitably configured and dimensioned to induce lateral capillary flow in the manner previously discussed. According to this version, the substrate 102 is preferably manufactured from an optically transparent plastic material.

The herein described cartridge 140 includes an upper cover portion 144 and a lower cover portion 148, each sized and configured to sandwich the lateral flow assay device 100 therebetween. The upper cover portion 144 includes a collection clip (not shown in this view) that acts as a sample supply or repository relative to a port 152 which is sized to permit the introduction of sample from the collection clip and aligned with the sample receiving zone 108 of the lateral flow assay device 100. This design creates a gated test element or cartridge in which sample is maintained within the collection clip until acted upon by a pump or similar means that drives the retained sample to the confines of the cartridge 140 to actuate the test element. According to this design, a separation filter 156 having a suitable porous surface is disposed either within or between the upper cover portion 144 and the sample receiving zone 108 of the lateral flow assay support 100. The lower cover portion 148 includes an elongated cavity 160 extending along substantially the length of the supported lateral flow assay device 100, enabling a detection instrument (not shown) to detect an analyte of interest in the at least one detection zone, typically using a fluorimeter that detects the degree of the detectable signal produced by the reagent.

Components of the lateral flow assay devices (i.e., a physical structure of the device whether or not a discrete piece from other parts of the device) described herein can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicone containing polymers, glass (such as etched glass), and ceramic materials. Alternatively, components of the device can be made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the lateral flow assay devices are injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

Figure 4A:
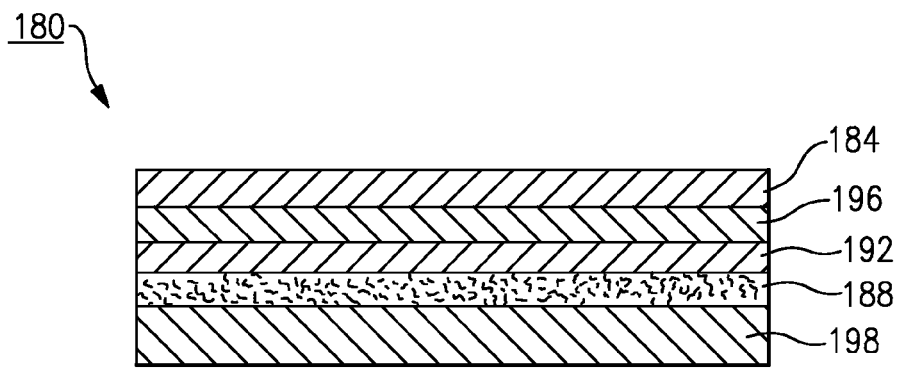
FIG. 4(a) is a sectional view of a known dry chemistry analytical test element.

In addition to lateral flow assay devices, there are also so-called "thin film" or dry slide chemistry analytical test elements that have been used extensively in main frame and desktop analyzers for determining certain analytes (markers) of interest. The basic principle of dry slide or thin film chemistry is described in U.S. Pat. No. 3,992,158, the entire contents of which are herein incorporated by reference. A typical sectioned view of a dry slide analytical test element 180 is shown in FIG. 4(a), in which a plurality of integral vertically stacked layers are disposed relative to a lower support 198. The layers include a spreading layer 184, such as a porous polymer, in fluid contact with at least one reagent layer 188 along with additional layers used to facilitate detection such as a reflecting layer 192 and a filtering layer 196, each of the foregoing layers being in stacked relation on the lower support 198. Detection of a test conducted on an dry slide analytical test element is conducted using a reflectometer to determine results based on changes to color density in regard to the reaction layer of the element or a potentiometer using dry chemistry test elements or slide elements having an ion selective electrode (not shown). Further details relating to the manufacture and testing of dry slide analytical elements are provided in the above incorporated '158 patent.

Figure 4B:
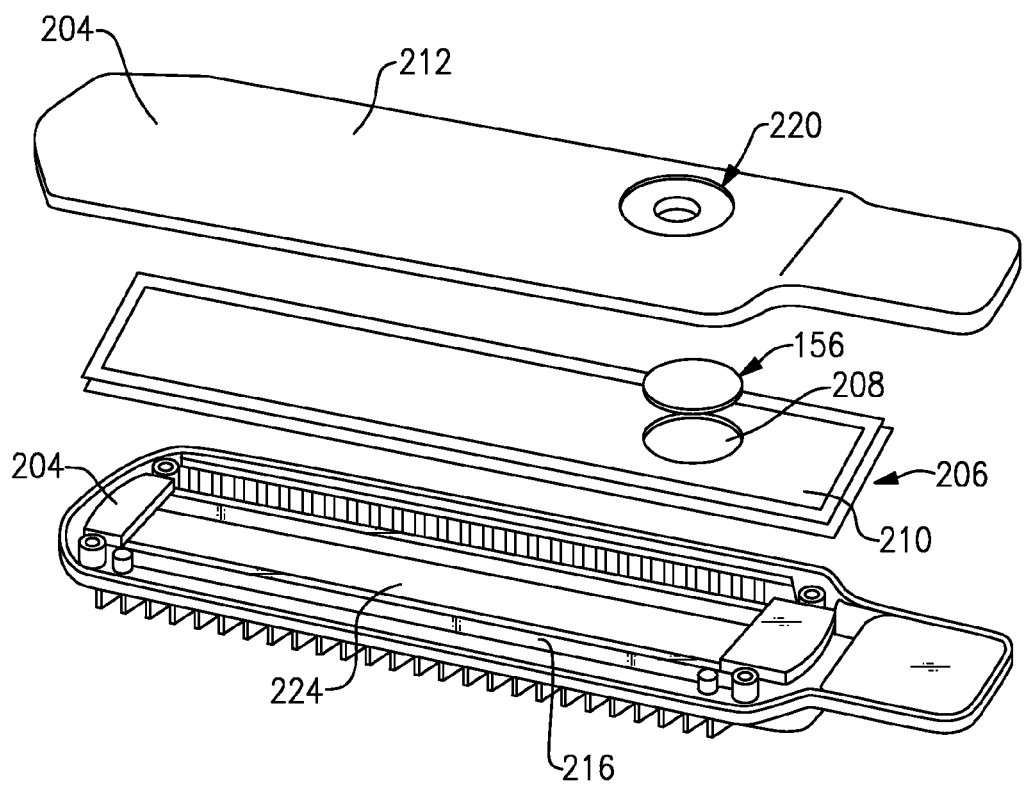
FIG. 4(b) is an exploded assembly view of a dry chemistry analytical test element incorporated into the cartridge of FIG. 3.

FIG. 4(b) illustrates an exemplary embodiment of an analytical test element in accordance with an exemplary embodiment. The analytical test element 200 comprises a cartridge 204 and a substrate or support 206 retaining at least one dry slide chemistry chip 208 that is supported relative to a top surface 210 of the support 206. The cartridge 204 comprises an upper cover portion 212 and a lower cover portion 216 that are fitted together and define an interior which is sized to retain the substrate 206 in fixed relation and in which the at least one chemistry chip 208 is disposed in relation to a sample dispensing port 220 provided on the upper cover portion 212 of the cartridge 204. According to this version, the chemistry chip 208 utilizes a so-called "dry slide" or "dry chemistry" format and in which a spreading layer of the chip 208 is aligned with the sample dispensing port 220 as well as an intermediate separation filter 156. The lower portion 216 of the cartridge 204 includes an elongated cavity 224 that permits use of a detection instrument such as a reflectometer to discern changes in color density of a reaction layer of the chip 208. Further details relating to the construction and salient features of a dry chemistry chip is provided in the previously incorporated U.S. Pat. No. 3,992, 158.

Figure 5:
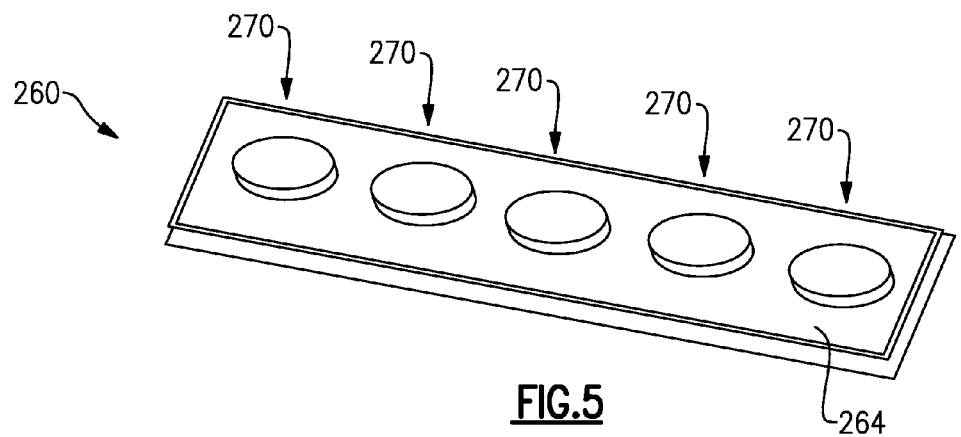
FIG. 5 is a perspective view of a multiplexed dry chemistry test support.

According to another exemplary embodiment, the above substrate/support can be suitably configured to retain more than one dry chemistry chip. In that regard, FIG. 5 illustrates an exemplary chemistry chip 260 that can be supported by a cartridge (not shown) similar to those previously described. According to this design, a plurality of separate dry chemistry chips 270 are disposed on a single planar substrate or support 264 in a linear arrangement that enables multiple tests to be conducted either sequentially or all at one time. This specific version includes five (5) dry chemistry chips that are disposed in spaced relation on the substrate 264, although it will be readily apparent this number can be suitably varied, if needed, depending on application/use.

Still further versions of an analytical test element can be contemplated. For example and according to FIG. 6, a support 304 for a combined or hybridized analytical test element 300 is depicted, this support 304 further enabling both a lateral flow assay device 320, such as shown in FIG. 2, as well as at least one dry chemistry chip 360, such as shown in FIG. 4(a), to be commonly supported. In this version, the support 304 comprises a planar substrate, which is made from a non-porous material such as a plastic or similar material. A sample receiving area or zone 308 is disposed at one end of a defined fluid flow path of the support 304, the sample receiving zone 308 extending to a reagent area or zone 312 that further extends to an absorbing or wicking area or zone 320 at the opposing end of the fluid flow path. A flow channel 316 interconnects the reagent area 312 and the absorbing zone 320, wherein the flow channel 316 also includes at least one detection area or zone 324. Each of the foregoing elements are common to a lateral flow assay device, such as previously described in FIG. 2. A plurality of flow control elements, such as projections (not shown) can be provided in each of the above disposed zones and the flow channel 316 to facilitate fluidic flow in the support 304 wherein the projections are configured with respect to each other and dimensioned in order to induce lateral capillary flow along the defined fluid flow path.

In addition and according to this exemplary embodiment, a pair of dry chemistry chips 360 are also provided on the support 304, each of the dry chemistry chips 360 including a preferably porous spreading layer and at least one reagent layer in vertically stacked relation to one another and in which the layers are disposed upon or within the planar substrate. The dry chemistry chips 360 and more specifically the porous spreading layer thereof is interconnected with the sample receiving zone 308 by means of respective flow channels 364, 368 which can be, for example, flow capillaries. Similar to the above described exemplary analytical test elements, the herein described support 304 can be used with a cartridge 140, FIG. 3, having an upper cover portion 144, FIG. 3, and lower cover portion 148, FIG. 3, sized to enclose the support 304 and in which the sample receiving area 308 is aligned with a fluid metering port 152, FIG. 3, and in which a separating cover 156, FIG. 3, is further provided beneath the metering port 152. As in the preceding, the cartridge 140, FIG. 3, is preferably further equipped with a collecting clip (not shown) that acts as a sample repository or supply until acted upon to direct the sample into the confines of the cartridge.

In terms of operation a sample such as a whole blood sample from a subject from a finger puncture is initially applied to the test element and more particularly the collecting clip, which retains the sample until the test element is actuated. Alternatively, a sample can be directly applied such as using a pipette or other means to the metering port 152, FIG. 3, In either instance and when sample is applied, the sample is separated through the filter and received by the sample receiving zone 308 of the support 304 and caused to move under capillary action to the adjacent reagent zone of the lateral flow assay device portion of the support 304. In addition, sample fluid is also caused to move from the sample receiving zone 308 via the flow channels 364, 368 to the respective dry chemistry chips 360 also under capillary force or by external means, such as a pump (not shown). When sample has filled the projections of the absorbing area 320, the lateral flow assay is deemed to be complete and a detection instrument (e.g., a fluorimeter) can be used to scan the detection area 324. Similarly, the reaction layer of the dry chemistry chips 360 creates a color density in proportion to the analyte of interest. The results can be measured by a reflectometer in which results can be calculated via appropriate mathematical models and calibration parameters. In each instance, the cartridge retaining the support 304 can include an elongated cavity to facilitate detection.

The foregoing construction of an analytical test element creates a form factor that is common to the previously described lateral flow assay device cartridge and therefore enables at least two different test and measurement/detection protocols to share a common interface to an analytical instrument. A reader containing the appropriate reflectometer and fluorimeter measurement instruments, can therefore process both lateral flow and dry chemistry assays, and thereby eliminate the need for multiple readers.

The foregoing common form factor designs are intended to be exemplary and that one of sufficient skill in the field could conceive of alternative versions embodying these inventive concepts.

The common form factor provided by the analytical test element described herein or equivalent structure advantageously enables a point of care (POC) analytical system having a larger and more extensive menu breadth. The ability of the POC reader to process more than one test at a time provides significant user benefit in terms of access availability (lack of backlog) and processing throughput (more results available and broader application to POC and hospital laboratory settings).

Moreover, the use of the collecting clip or similar structure enables the cartridge to be "gated"; that is, the sample can be accessed selectively for purposes of actually performing a test(s).

Figure 7:
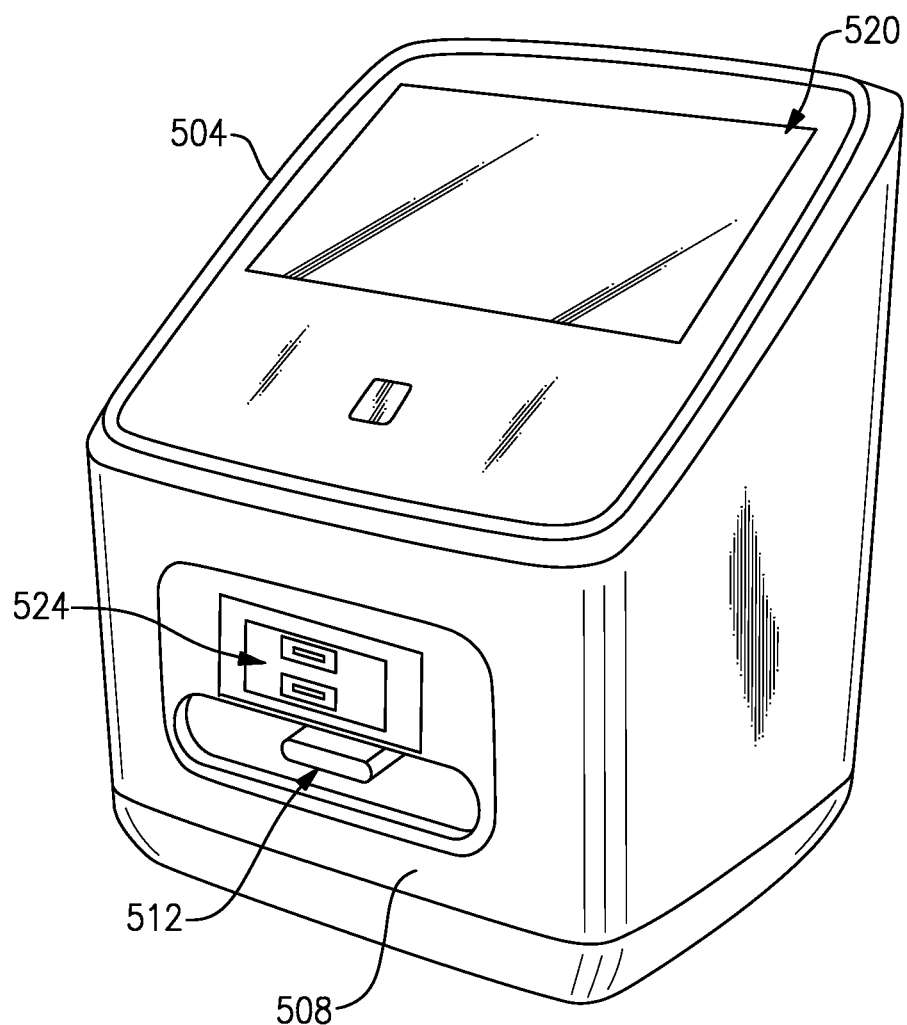
FIG. 7 is a front perspective view of a point of care reader in accordance with an exemplary embodiment.

Referring to FIG. 7, there is shown a point of care (POC) reader 500 in accordance with an exemplary embodiment that is configured to utilize the herein described analytical test elements, the reader 500 being configured to enable multiple tests and test (measurement) methods as well as random access.

More specifically and according to this exemplary embodiment, the reader 500 is defined by a compact housing 504 having an entry/exit port 512 provided along a front side 508 of the housing 504 to permit individual loading and unloading of analytical test elements such as those previously described and depicted in FIGS. 3-6. Optionally, a stacker port 524 is also provided adjacent the entry/exit port 512 on the front side 508 in order to position a quantity of cartridges for processing all at one time. A display 520 is also provided that includes a touch screen, providing a user interface for the device 500. The system or the reader 500 may further include a bar code reader (not shown) in which the reader 500 can be powered by contained batteries (not shown) or using an AC power source (not shown). A cartridge that retains a plurality of test elements can include an encoded label indicative of the type of test to be performed using the test elements in which the label can be read and a contained processor is configured to automatically engage the encoded label without user intervention.

Figure 8:
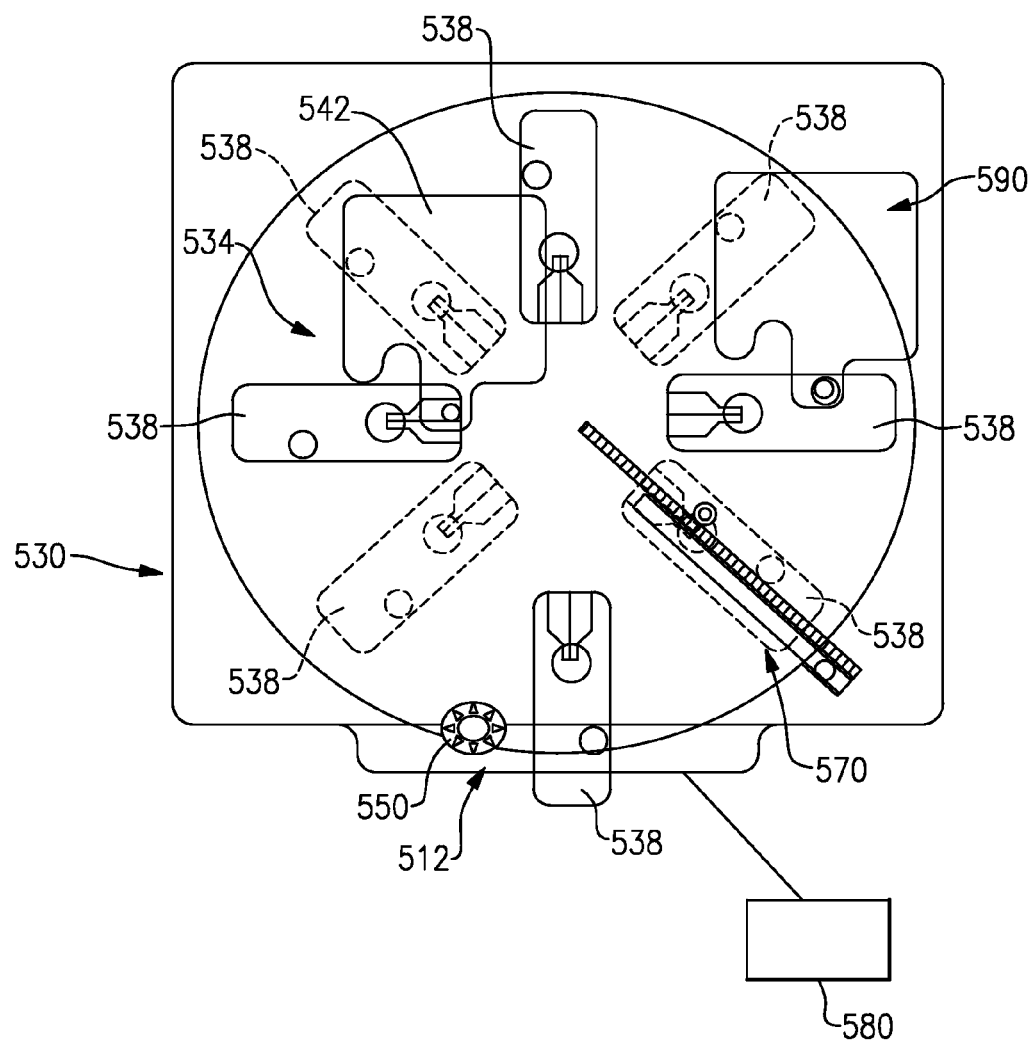
FIG. 8 is a partial top view, taken in section, of the interior of the point of care reader of FIG. 7.

FIG. 8 illustrates an exemplary embodiment of the interior of the reader 500 of FIG. 7. More specifically, an incubator 530 is disposed within the interior of the reader housing 504, FIG. 7, the incubator 530 including a rotatable rotor 534 having a plurality of circumferentially disposed slots 538, each slot 538 being sized to retain an analytical test element, such as those previously described according to FIGS. 4-6 and permit access by at least one detection instrument. The rotor 534 consists of N positions or slots 538 in which N can be 1, 2-8, or more. In this version, a total of eight (8) slots 538 are depicted, with four (4) of the slots 538 being shown in phantom. Each circumferentially disposed slot 538 is configured and sized to support an active test cartridge for processing immunoassays or general chemistry. The incubator rotor 534 can be driven by a mechanism 550, shown schematically, which can include a belt, magnetic, gear driven or other suitable apparatus configured to selectively engage the rotatable rotor 534 for rotation about a center vertical axis.

Various modules are positioned at specific stations disposed within the housing 504 and relative to the periphery of the rotatable rotor 534 so as to access the circumferentially disposed slots 538 of the incubator 530. More specifically and according to this embodiment, a metering station 542 supports a sample infusion pump or other suitable mechanism that is configured to engage the collecting clip of a supported cartridge and apply fluidic pressure that causes the retained sample to be moved through the filter and to the sample receiving area of the analytical test element. The incubator 530 can be indexed by means of the drive mechanism 550 to sequentially advance or index the rotor 534 and align an analytical test element, and more specifically the collecting port of the test element with the infusion pump for engagement therewith. Alternatively, a pipette or similar dispensing means can be provided in lieu of the infusion pump. In either event, the metering station 542 is configured to selectively apply sample or move retained sample to the sample addition area of a cartridge when a gated test element is aligned properly. Sensors (not shown) can be provided to detect whether a test element is present within the slot 538 and is correctly located or positioned relative to the pump, the sensors being connected to a resident controller 580 (shown schematically in this view). If a slot 538 is empty or a test cartridge is not properly oriented within the slot 538, the pump or other dispensing means is not activated and an error message is presented on the display 520 to the user.

Additionally, at least one measurement module 570 is further provided within the interior of the reader housing 504, in relation to the incubator rotor 534 and more specifically aligned with the circumferentially disposed slots 538. According to this specific embodiment, the measurement module 570 includes a scanning reflectometer as well as a fluorimeter, each of which are configured to traverse along a defined scan path. Other measurement modules can be additionally or alternatively disposed in relation to the incubator 530 such as a potentiometer to measure ion selective electrode potentiometric chemistry, a photometer, or other suitable measurement instrument, each enabled based on a testing protocol selected by a user and stored by the controller 580.

According to this specific embodiment, a wash module 590 is also disposed relative to the incubator 530. The wash module 590 is interconnected to the controller 580 and is configured and aligned to automatically apply a quantity of wash fluid to a retained test element, such as a lateral flow assay device, based on a testing protocol stored by the resident controller 580.

In terms of overall operation, a plurality of analytical test elements (cartridges) can be individually loaded into the reader 500 through the input port 512 in which the incubator 530 is indexed (i.e., 45 or 90 degrees) by the drive mechanism 550 to enable loading of a predetermined number of analytical test elements into the various slots 538 of the rotor 534. The test elements that are loaded can include any or all of the various exemplary test element designs previously discussed and include at least one lateral flow assay device, dry chemistry chip(s) or a combination of each. According to another version, at least one cartridge can be placed in the stacker port such that the cartridge is not immediately loaded into the reader 500, but which is configured for loading at a later time. In one version, the system includes at least one pusher blade or similar transport mechanism (not shown) that is configured to engage the cartridge of the test element and pull the cartridge into an empty slot 538 of the incubator 530.

A specific testing protocol can be established by accessing a menu on the touch screen of the display 520 using the user interface of the reader 500, in which the protocol is controlled automatically by the controller 580. Alternatively, the analyzer can utilize bar code reader to scan a loaded cartridge containing test elements in order to ascertain the type of test(s) to be conducted automatically without user intervention being required. Still further, the test element or cartridge(s) can include machine readable tags, such as RFID tags. Results obtained by the reader 500 can be displayed and further can be transmitted either or a wired connection or wirelessly to a remote location using WiFi, Bluetooth or other wireless protocol. The selection of various testing protocols can be established depending on whether the analytical test elements loaded are of the traditional lateral flow assay device design, an analytical dry slide element design and/or a hybrid design having each.

A typical or exemplary testing protocol is now described. First, an analytical test element is accessed wherein a sample is taken using a finger stick or other means and in which the sample is added to the collection clip of the cartridge. Details relating to the collection clip can be found in U.S. Patent Application Publication No. 2014/0275866 A1, entitled: Rotatable Disk-Shaped Fluid Sample Collection Device, filed Mar. 13, 2014 and U.S. Pat. No. 9,678,069 B2, entitled: Rotatable Fluid Sample Collection Device, granted Jun. 13, 2017, the entire contents of which are herein incorporated by reference. The cartridge can further include a label that can be scanned by a bar code reader in which the label information identifies the specific test element and the test to be conducted therewith. This information can be presented on either the display 520 of the reader 500 and/or the bar code reading device. The operator can then enter specific information to the display/touch screen 520 relating to the patient, demographics or other pertinent information that is stored by the controller 580. Upon completing the entries, a button either on the reader housing 504 or the display 520 can be actuated by the operator. At this stage, the operator's involvement with the system is complete, assuming all cartridges have either been loaded within the input/exit slots 512 or the stacker slot 524 of the housing 504.

Based on the stored protocol by the controller 580, an analytical test element can then either be loaded from the stacker slot 524 and indexed or an already loaded test element can be indexed by the drive mechanism 550 to move a predetermined incubator slot 538 to the metering station 542.

Once aligned with the metering station 542 and upon sensing the presence of the analytical test element, the infusion pump is brought into contact with the collecting clip of the test element and the pump delivers a pressure differential that enables sample to be directed to the separation filter and the sample receiving area of the test element. The actuation of the infusion pump (or other dispensing or metering apparatus) can also automatically initiate a timer (not shown).

Figure 6:
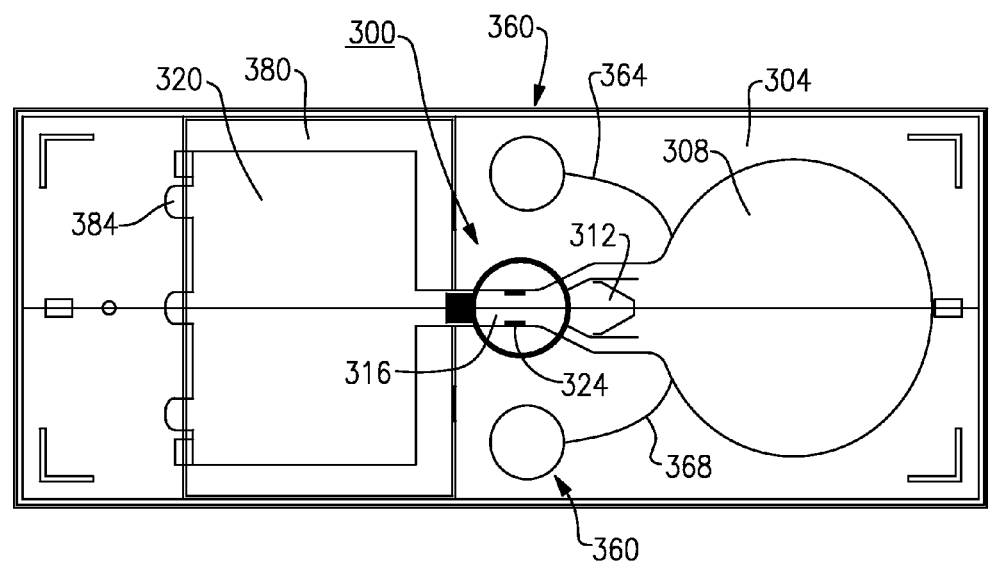
FIG. 6 is a top plan view of an exemplary test support in accordance with another embodiment incorporating both a lateral flow assay device and a plurality of dry chemistry test chips.

Filtered sample is then directed along the contained support of the test element from the sample receiving area to the various test areas. In the case of a dry chemistry chip, fluid is moved such as shown in FIG. 6 from the sample receiving area through flow channels to the porous spreading layer of the dry chemistry chips wherein the spread sample permeates to the at least one reagent layer. In the case of a lateral flow assay device, sample is directed to an adjacent reagent area to wet a deposited detection material and in which sample and dissolved detection material is moved along the defined fluid flow path of the device through a flow channel having at least one detection zone and an absorbing area. As noted, a varied number of tests can be conducted via a single cartridge.

Timing for a colorimetric testing of a typical dry chemistry chip is on the order of about five (5) minutes, while time to complete a lateral flow device assay is on the order of about 10-15 minutes. As a result, it may be possible depending on the analytical test element used to advance the test element to the measurement station 570 after five minutes while still being incubated in order to use the reflectometer to determine the colorimetric results of the dry chemistry tests. At the same time and according to at least one version, the fluorimeter can also scan the test element to determine the progress of the lateral flow assay by detecting the location of the conjugate plume created by the sample and dissolved detection material. Each of the results obtained can be compared to stored values and/or ranges to determine, for example, a test failure resulting from a test or manufacturing flaw and thereby permit early termination of a testing protocol by the system.

Otherwise, testing continues and in which other test elements have been indexed to the metering station 542, the test element can be indexed to the wash module 590 wherein a wash fluid can be added to the test element to flush the detection material and sample prior to detection by the measurement module 570.

Upon completion of the predetermined timing interval to conduct the test, the reader 500 is configured to eject the analytical test element. The use of gated cartridges employing a common form factor and the ability to conduct multiple tests simultaneously provides significant benefits and advantages, as compared to earlier known systems.

Advantageously and assuming a conventional test requires a time interval of approximately 12 minutes to complete, a single prior art reader using tests such as shown according to FIG. 1 would have an effective throughput of 5 tests per hour. By way of comparison, a reader 500, FIG. 8, that has an incubator 530 configured with eight slots 538, would achieve a throughput of about 96 tests per hour. Moreover and if the test elements include multiple test chips such as shown in FIG. 5 or 6 thereon, the throughput metrics further increase. For example and assuming a single test element is configured to conduct 8 separate tests, the throughput can be increased to about 768 tests per hour. Similarly, a reader having a rotor (not shown) having four (4) slots (not shown), would have a throughput of about 384 tests per hour.

PARTS LIST FOR FIGS. 1-8

1 lateral flow assay device
2 sample receiving zone
3 reagent zone
4 flow channel
5 absorbing or wicking zone
6 substrate
7 top surface
12 projections
20 lateral flow assay device
40 substrate
44 top or upper surface
48 sample receiving zone
52 reagent zone
56 detection zone(s)
60 absorbing zone
64 flow channel
70 hydrophilic foil or tape cover
74 vent areas
100 lateral flow assay device
102 support or substrate
104 top or upper surface
108 sample receiving zone
112 reagent zone
118 detection zone(s)
120 flow channel
140 cartridge
144 upper cover portion
148 lower cover portion
152 port
156 separation filter
160 elongated cavity
180 dry slide or thin film analytical test element
184 spreading layer
188 reagent layer
192 reflecting layer
196 filtering layer
198 support
200 analytical test element
204 cartridge
206 substrate or support
208 dry slide chemistry chip
210 top surface
212 upper cover portion
216 lower cover portion
220 port, dispensing
224 elongated cavity
260 analytical test element support
264 substrate
270 dry chemistry chips
300 analytical test element
304 support
308 sample receiving area or zone
312 reagent area or zone
316 flow channel
320 absorbing or wicking area
324 detection area or zone
360 dry chemistry chips
364 flow channel
500 reader, point of care
504 housing, reader
508 front side, housing
512 entry/exit port
520 display
524 stacker port
530 incubator
534 rotatable rotor
538 slots, incubator
542 metering station
550 drive mechanism
570 measurement station
580 controller
590 wash module It will be readily apparent that other versions and modifications can be made in accordance with the inventive concepts discussed herein as well as according to the following claims. In addition, separate references are made throughout to "an embodiment", or "an exemplary embodiment", or "a specific embodiment" or "at least one version". These references do not necessarily refer to the same embodiment or embodiments; however, such embodiments or versions are also not mutually exclusive, meaning that the features described throughout as pertaining to the various test elements and devices can be combined in various permutations to include some or all of the embodiments and versions.

The invention claimed is:

1. A point of care analytical testing system comprising:
   a point of care reader comprising:
   a housing having an interior;
   an incubator disposed in the housing interior and having a rotor configured for rotation, the incubator having a plurality of circumferentially disposed slots;
   a drive mechanism for rotating the rotor about a center axis; and
   at least one measurement device disposed within the housing, the at least one measurement device being movable along a defined scan path; and
   a plurality of analytical test elements, each analytical test element being sized for fitting in a slot of the incubator and comprising:
   a planar support; and
   a cartridge sized for retaining the planar support, the cartridge comprising an upper cover portion and a lower cover portion that supports ends of the planar support and has an elongated axial cavity over which the planar support is supported, the upper cover portion including at least one port configured for applying a quantity of sample to the retained support and wherein the planar support retains at least one of a dry chemistry chip comprising a porous spreading layer disposed in stacked relation with at least one reagent layer or a lateral flow assay device, wherein the elongated axial cavity enables the at least one measurement device to measure the sample by movement along the defined scan path.

2. The system according to claim 1, in which at least one of the analytical test elements is configured to run a plurality of tests.

3. The system according to claim 1, wherein the at least one port of the cartridge is configured for applying a quantity of sample to a sample receiving zone of the support.

4. The system according to claim 3, wherein the at least one port is aligned with the sample receiving zone of the support and in which the sample receiving zone is common to each of the lateral flow assay device and the at least one dry chemistry chip.

5. The system according to claim 4, including a separation filter disposed between the at least one port and the sample receiving zone.

6. The system according to claim 1, wherein the cartridge further includes a sample retainer, the sample retainer being configured to selectively release retained sample to the planar support.

7. The system according to claim 6, in which the reader includes a sample metering station disposed in relation to the incubator.

8. The system according to claim 7, wherein the sample metering station includes a pump enabled to apply pressure to move sample from the sample retainer to a sample receiving zone of the test element.

9. The system according to claim 1, wherein the at least one measurement device includes at least one of a reflectometer, photometer, fluorimeter, potentiometer, an imager and an infrared sensor.

10. The system according to claim 1, wherein the reader further comprises a wash module.

11. The system according to claim 1, comprising a controller connected to a user interface and the reader, the controller being programmed to operate the reader in accordance with at least one stored set of instructions.

12. The system according to claim 11, wherein the reader further comprises a display, the display including the user interface.

13. The system according to claim 1, wherein the reader includes at least one input/exit port for loading and unloading the analytical test elements.

14. The system according to claim 13, wherein the reader includes a stacker port configured to automatically load at least one analytical test element into the reader.

\* \* \* \* \*